United States Patent
LaFontaine

(10) Patent No.: US 7,850,681 B2
(45) Date of Patent: *Dec. 14, 2010

(54) CRYOPLASTY DEVICE AND METHOD

(75) Inventor: Daniel M. LaFontaine, Plymouth, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1305 days.

This patent is subject to a terminal disclaimer.

(21) Appl. No.: 11/357,938

(22) Filed: Feb. 17, 2006

(65) Prior Publication Data

US 2006/0178663 A1 Aug. 10, 2006

Related U.S. Application Data

(60) Continuation of application No. 10/659,116, filed on Sep. 10, 2003, now Pat. No. 7,022,120, which is a continuation of application No. 09/916,147, filed on Jul. 25, 2001, now Pat. No. 6,648,878, which is a continuation of application No. 09/229,080, filed on Jan. 12, 1999, now Pat. No. 6,290,696, which is a division of application No. 08/812,804, filed on Mar. 6, 1997, now Pat. No. 5,868,735.

(51) Int. Cl.
*A61B 18/18* (2006.01)

(52) U.S. Cl. .......................... 606/20; 606/21
(58) Field of Classification Search ........... 606/20–26
See application file for complete search history.

(56) References Cited

U.S. PATENT DOCUMENTS

| | | | |
|---|---|---|---|
| 3,125,096 A | 3/1964 | Antiles et al. | |
| 3,712,306 A | 1/1973 | Bryne | |
| 4,278,090 A | 7/1981 | Van Gerven | |
| 4,280,499 A | 7/1981 | Sguazzi | |
| 4,784,133 A | 11/1988 | Mackin | |
| 4,860,744 A | 8/1989 | Johnson et al. | |
| 5,019,042 A | 5/1991 | Sahota | |

(Continued)

FOREIGN PATENT DOCUMENTS

EP 1019028 2/1996

(Continued)

OTHER PUBLICATIONS

Abstract entitled "Argon Beam Coagulation Compared with Cryoablation of Ventricular Subendocardium," *Annals of Thoracic Surgery*, Jan. 1993, 1 page.

(Continued)

*Primary Examiner*—Roy D Gibson
(74) *Attorney, Agent, or Firm*—Crompton, Seager & Tufte, LLC

(57) ABSTRACT

A cryoplasty catheter and method for preventing or slowing reclosure of a lesion following angioplasty. The cryoplasty catheter includes a shaft having proximal and distal ends and a dilatation balloon disposed at the distal end. An intake lumen and exhaust lumen are defined by the shaft to deliver coolant to the balloon and to exhaust or drain coolant from the balloon. The method in accordance with the present invention includes cooling a lesion to aid in remodeling the lesion through dilatation and/or freezing a portion of the lesion adjacent the dilatation balloon to kill cells within the lesion to prevent or retard restenosis.

15 Claims, 2 Drawing Sheets

U.S. PATENT DOCUMENTS

| | | | |
|---|---|---|---|
| 5,078,713 | A | 1/1992 | Varney |
| 5,108,390 | A | 4/1992 | Potocky et al. |
| 5,139,496 | A | 8/1992 | Hed |
| 5,147,355 | A | 9/1992 | Friedman et al. |
| 5,190,540 | A | 3/1993 | Lee |
| 5,281,215 | A | 1/1994 | Milder |
| 5,334,181 | A | 8/1994 | Rubinsky et al. |
| 5,334,193 | A | 8/1994 | Nardella |
| 5,335,669 | A | 8/1994 | Tihon et al. |
| 5,342,301 | A | 8/1994 | Saab |
| 5,417,653 | A * | 5/1995 | Sahota et al. .......... 604/20 |
| 5,417,689 | A | 5/1995 | Fine |
| 5,423,807 | A | 6/1995 | Milder |
| 5,443,470 | A | 8/1995 | Stern et al. |
| 5,454,807 | A | 10/1995 | Lennox et al. |
| 5,501,681 | A | 3/1996 | Neuwirth et al. |
| 5,520,682 | A | 5/1996 | Baust et al. |
| 5,536,252 | A | 7/1996 | Imran et al. |
| 5,624,392 | A | 4/1997 | Saab |
| 5,957,917 | A | 9/1999 | Doiron et al. |
| 5,971,979 | A | 10/1999 | Joye et al. |
| 6,012,457 | A | 1/2000 | Lesh |
| 6,024,740 | A | 2/2000 | Lesh et al. |
| 6,355,029 | B1 | 3/2002 | Joye et al. |
| 6,428,534 | B1 | 8/2002 | Joye et al. |
| 6,432,102 | B2 | 8/2002 | Joye et al. |
| 6,468,297 | B1 | 10/2002 | Williams et al. |
| 6,595,988 | B2 | 7/2003 | Wittenberger et al. |
| 6,706,037 | B2 | 3/2004 | Zvuloni et al. |
| 6,755,823 | B2 | 6/2004 | Lalonde |
| 6,796,979 | B2 | 9/2004 | Lentz |
| 6,893,433 | B2 | 5/2005 | Lentz |
| 6,981,382 | B2 | 1/2006 | Lentz et al. |
| 2003/0088240 | A1 | 5/2003 | Saadat |

FOREIGN PATENT DOCUMENTS

| | | |
|---|---|---|
| WO | WO 00/47118 | 8/2000 |

OTHER PUBLICATIONS

Abstract entitled "Cardiac Rhythm Disturbances due to Caval Occlusion During Hepatic Cryosurgery," *Cryobiology*, Oct. 1994, 1 page.

Abstract entitled "Cox Maze Operation Without Cryoablation for the Treatment of Chronic Atrial Fibrillation," *Annals of Thoracic Surgery*, Aug. 1995, 1 page.

Abstract entitled "Histologic Study of Chronic catheter Cryoablation of Atrioventricular Conduction in Swine," *American Heart Journal*, Jun. 1993, 1 page.

Abstract entitled "Intractable Chest Pain in Cardiomyopathy: Treatment by a Novel Technique of Cardiac . . . ," *British Heart Journal*, Dec. 1993, 1 page.

Abstract entitled Percutaneous Serial Catheterization in Swine: a Practical Approach,: *Journal of Investigative Surgery*, Mar.-Apr. 1995, 1 page.

Abstract entitled "Renal Cryoablation in a Canine Model," *Urology*, May 1996, 1 page.

Article entitled "Prostrate Cryosurgery now Reimbursable in Southern California," *Healthcare Technology Management*, published on date even with or prior to Jan. 12, 1999.

Cahan, "Five Years of Cryosurgical Experience: Benign and Malignant Tumors with Hemorrhagic Conditions," *Cryosurgery*, published on date even with or prior to Jan. 12, 1999, pp. 388-391.

Coger et al., "Preservation Techniques for Biomaterials," *The Biomedical Engineering Handbook*, 1995, pp. 1567-1577.

Fuller et al., "Clinical Applications of Cryobiology," 4 pages, published on date even with or prior to Jan. 12, 1999.

Hunt et al., "Fractures in Cry opreserved Arteries," *Cryobiology*, 1994, 31:506-515.

Mazur, Physical-Chemical Factors Underlying Cell Injury in Cryosurgical Freezing, *Cryosurgery*, published on date even with or prior to Jan. 12, 1999, pp. 32-51.

Morris et al., "Effects of Low Temperatures on Biological Membranes," 2 pages, published on date even with or prior to Jan. 12, 1999.

Nataf et al., "Effect of Cold Anoxia and Cryopreservation on Metabolic and Contractile Functions of Human Mammary Artery," *Cryobiology*, 1995, 32:327-333.

Schilling et al., "Nature of the Vehicle for Cryopreservation of Human Peripheral Veins: Preservation of Reactivity to Pharmacological Stimuli," *Cryobiology*, 1995, 32:109-113.

Stephenson et al., "Renal Cryoablation in a Canine Model," *Urology*, 1996, 47(5):772-776, Abstract only.

Zacarian, "Cryosurgery of Tumors of the Skin and Oral Cavity," 5 pages, published on date even with or prior to Jan. 12, 1999.

* cited by examiner

CRYOPLASTY DEVICE AND METHOD

CROSS REFERENCE TO RELATED APPLICATIONS

This application is a continuation of U.S. application Ser. No. 10/659,116, filed Sep. 10, 2003 now U.S. Pat. No. 7,022,120; which is a continuation of U.S. application Ser. No. 09/916,147, filed Jul. 25, 2001 and issued as U.S. Pat. No. 6,648,878 on Nov. 18, 2003; which is a continuation of U.S. application Ser. No. 09/229,080, filed Jan. 12, 1999 and issued as U.S. Pat. No. 6,290,696 on Sep. 18, 2001; which is a divisional of U.S. application Ser. No. 08/812,804, filed Mar. 6, 1997 and issued as U.S. Pat. No. 5,868,735 on Feb. 9, 1999, the contents of which are hereby incorporated by reference.

FIELD OF THE INVENTION

The present invention pertains generally to the field of angioplasty and, in particular, to a form of angioplasty involving lesion cooling.

BACKGROUND

Conventional angioplasty has been preformed for several decades, prolonging the lives of an ever increasing number of patients. Angioplasty procedures involves the dilatation of a balloon placed across a lesion in a coronary artery. Dilatation of the balloon in turn dilates the lesion, opening the artery for increased blood flow. In some cases, however, the goal of the angioplasty procedure is, in whole or in part, frustrated by complete or partial reclosure of the artery at the lesion. Two mechanisms are believed to be principally responsible for reclosure of the artery, these are restenosis and recoil. Restenosis is believed to be caused by continued growth or regrowth of the smooth muscle cells associated with the lesion. Recoil is in part a mechanical process involving elastic rebound of the dilated lesion.

Several means have been disclosed for addressing the problem of restenosis. These include, among others, radiation treatments to slow or prevent smooth muscle cell proliferation associated with the restenotic process. Certain drug therapies have been proposed to prevent or slow restenosis.

Several means have also been developed to address the issue or recoil. One of the more significant developments in this area has been stents, which can be permanently deployed to mechanically hold open lesions. Although stents have been found to be highly effective, they may irritate the wall of a artery in which they are implanted. Some believe that this may encourage limited restenosis. Warming of the lesion during dilatation has also be disclosed to prevent or slow recoil. Warming the lesion is believed to soften the lesions such that it may be "remodeled" that is, thinned under low pressure. Heating of the lesion, however, is believed to cause an injury response which may cause some restenosis.

SUMMARY OF THE INVENTION

The present invention is directed at an apparatus and method for performing angioplasty and preventing or slowing the post-procedure reclosure of dilated lesion. The present invention cools the lesion to prevent or slow reclosure by the mechanisms of restenosis or recoil. A cryoplasty catheter is provided to cool the lesion to aid in remodeling the lesion to prevent or slow recoil. The present invention can also be used to cool the lesion to freeze a portion of the lesion tissue. This is believed to kill cells within the lesion which would promote restenosis.

A preferred embodiment of the cryoplasty catheter in accordance with the present invention includes a shaft having proximal and distal ends. The shaft defines an inflation lumen, coolant intake lumen and exhaust lumen therethrough. Each lumen has a proximal and distal end proximate the proximal and distal ends of the shaft respectively. A dilatation balloon is disposed at the distal end of the shaft and is in fluid communication with the inflation lumen. A chamber is disposed within the balloon and is in fluid communication with the intake and exhaust lumens. A source of coolant is connected to the proximal end of the shaft in fluid communication with the coolant intake lumen.

A thermo-resistive sensor can be disposed on the dilatation balloon to monitor the temperature of the lesion. A second thermo-resistive sensor can be disposed on the shaft to provide a control temperature reading.

In another preferred embodiment of the cryoplasty catheter in accordance with the present invention, the cryoplasty catheter includes a shaft having proximal and distal ends. The shaft defines an inflation lumen and a drain lumen therethrough. Each lumen has a proximal and a distal end proximate the proximal and distal ends of the shaft respectively. A dilatation balloon is disposed at the distal end of the shaft and is in fluid communication with the inflation and drain lumens. The cryoplasty catheter also includes a coolant source connected to the proximal end of the shaft in fluid communication with the inflation lumen.

This embodiment of the cryoplasty catheter can also include a thermo-resistive sensor disposed on the dilatation balloon. As well as the thermo-resistive sensor disposed on the balloon, a control sensor can be disposed on the catheter shaft.

A method of performing cryoplasty is also provided which includes the steps of advancing the cryoplasty catheter across a lesion, inflating the dilatation balloon to dilate the lesion, and delivering coolant to the balloon to cool the lesion. To aid in remodeling, the lesion adjacent the balloon can be cooled to between 10° C. and −10° C. A portion of the lesion adjacent the balloon can also be frozen to kill cells within the lesion which would otherwise promote restenosis. For enhanced effectiveness, freezing may be done by flash freezing the tissue for 20 to 60 seconds. The cells are preferably frozen at a temperature of between −20° C. and to −40° C.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION OF THE INVENTION

Figure 1:
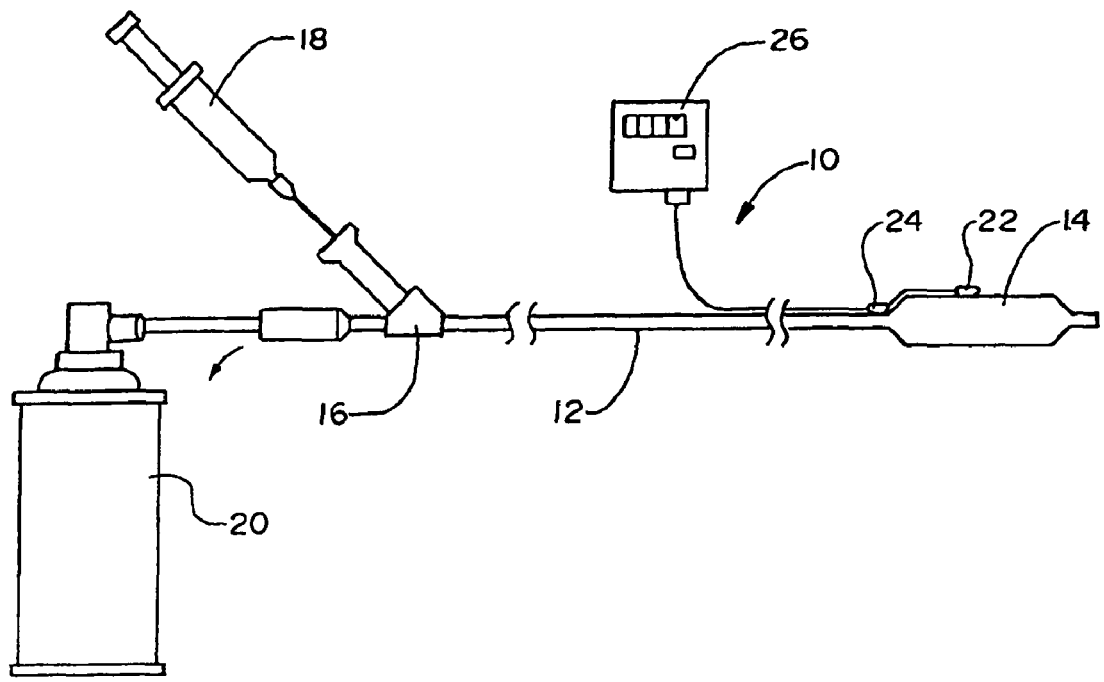
FIG. 1 is a side view of a cryoplasty catheter in accordance with the present invention.

Referring now the drawings wherein like reference numerals refer to like elements throughout the several views, FIG. 1 is a side view of a cryoplasty catheter 10 in accordance with the present invention. Shaft 12 has a proximal end and a distal end. A dilatation balloon 14 is disposed at the distal end of shaft 12. At the proximal end of shaft 12 is a manifold 16. Connected to manifold 16 is a pump 18, which can be hand pumped for inflating balloon 14. A coolant source 20 is also connected to manifold 16 which, as explained below, provides a supply of coolant to balloon 14. Catheter 10 can be provided with a thermo-resistive temperature sensor 22 for monitoring the temperature of a lesion and a thermo-resistive control sensor 24 connected to a monitor 26.

Figure 2:
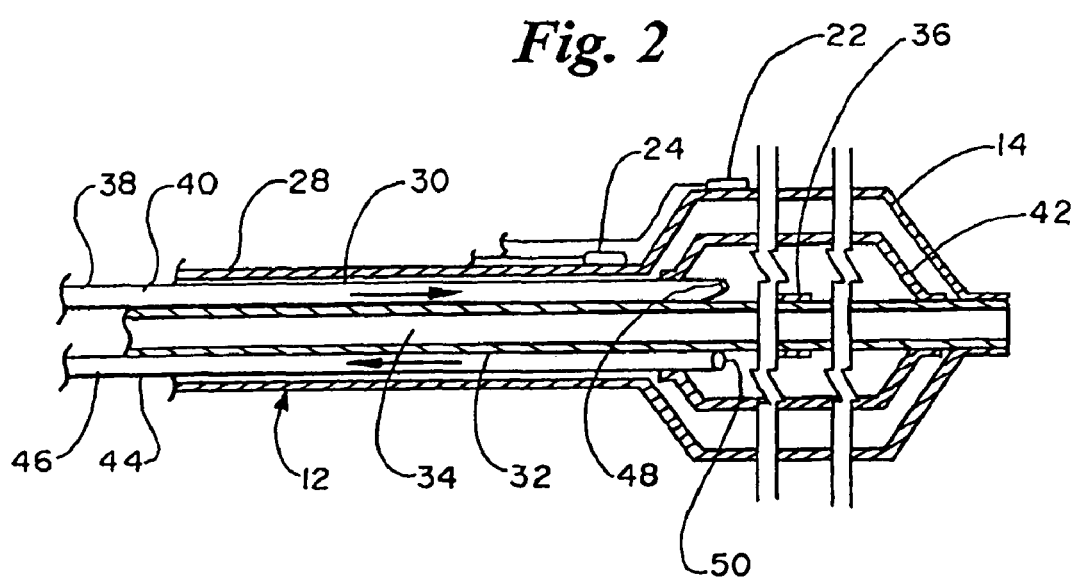
FIG. 2 is a longitudinal cross-sectional view of the distal end of the cryoplasty catheter of FIG. 1.

FIG. 2 is a longitudinal, cross-sectional view of the distal end of catheter 10 including the distal end of shaft 12 and balloon 14. Shaft 12 includes an outer tube 28 which defines an inflation lumen 30 in fluid communication with the interior balloon 14. A guidewire tube 32 defining a guidewire lumen 34 can extend through at least a portion of shaft 12 to distal of balloon 14. A marker ban 36 can be disposed on guidewire tube 32 within balloon 14.

Shaft 12 also includes a coolant intake tube 38 defining a coolant lumen 40 in fluid communication with a cooling a chamber 42 disposed within balloon 14. Shaft 12 also includes an exhaust or drain tube 44 which defines an exhaust or drain lumen 46 in fluid communication with chamber 42. At the distal end of tube 38 is an orifice 48 which preferably has a diameter smaller than that of an orifice 50 at the distal end of tube 44. The diameter of orifice 48 could be, for example, about 0.004 inches, or larger or smaller depending upon the diameter of orifice 50.

Those skilled in the art will recognize the various materials which can be advantageously used to make the catheter of the present invention. Those elements not found in conventional angioplasty catheter such as coolant intake tube 38, chamber 42 and exhaust tube 44 can also be made from materials known to those skilled in the art. For example, inlet tube 38 can be a hypotube or polyimide tube having an inside diameter of, for example, between 0.002 and 0.010 inches, but preferably between 0.002 and 0.10 inches. Exhaust tube 44 can be made from polyimide and have an inside diameter which is preferably greater than the inside diameter of inlet tube 38. The chamber 42 can be made from polyimide. These materials and dimensions should be viewed as exemplary only, as those skilled in the art would appreciate the applicability of alternative dimensions and materials for these elements.

Figure 3:
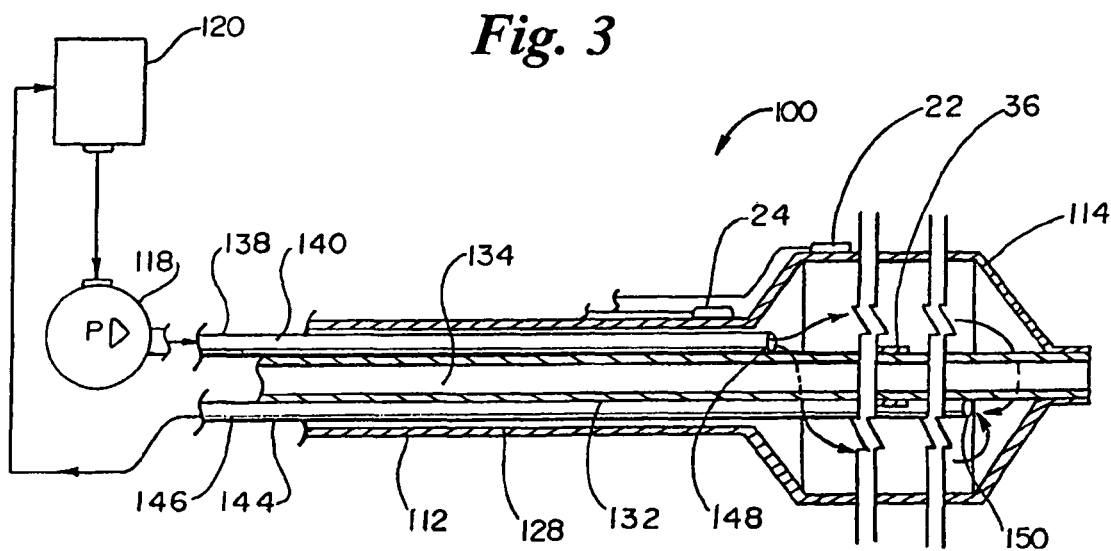
FIG. 3 is an alternate embodiment of a cryoplasty catheter in accordance with the present invention.

FIG. 3 is a schematic view of another embodiment of a cryoplasty catheter in accordance with the present invention referred to by the numeral 100. Cryoplasty catheter 100 includes a shaft 112 having a proximal distal end and a distal end. A balloon dilatation balloon 114 is disposed at the distal end of shaft 112. Proximate the proximal end of shaft 112 is a pump 118 connected to a coolant source 120 which can include refrigeration for controlling the temperature of the coolant.

A guidewire tube 132 defines a guidewire lumen 134 extending through at least a portion of shaft 112 to the distal end of catheter 100. A coolant intake/inflation tube 138 having a proximal end and a distal end proximate the proximal and distal ends of shaft 112 defines a coolant/inflation lumen 140. Lumen 140 is in fluid communication with pump 118 proximate its proximal end and balloon 114 proximate its distal end. Shaft 112 also includes an exhaust/drain tube 144 defining a lumen 146 and having a proximal and distal end proximate the proximal and distal ends of shaft 112, respectively. The distal end of lumen 146 is in fluid communication with balloon 114. The proximal end of lumen 146 can be in fluid communication with the coolant source 120 for recycling of coolant, or may be discharged for disposal. Lumen 140 has a distal orifice 148 which is preferably smaller than a distal orifice 150 of lumen 146.

Those skilled in the art will recognize that there are numerous materials and methods of manufacture which would be suitable for production of catheter 100. Those elements of catheter 100 which are not typical of angioplasty catheters such as inflation/intake tube 138 and exhaust/drain tube 144 can be made as described above with respect to the corresponding elements of catheter 10. It should be noted however that tube 138 should be sized appropriately to serve its dual purpose as an inflation tube and coolant intake tube. Additionally, the sizes of tubes 138 and 144, as well as the corresponding elements of catheter 10 should be sized to take into account the physical properties of a particular coolant medium for example, the relative rate of heat transfer to the coolant medium from a lesion.

Figure 4:
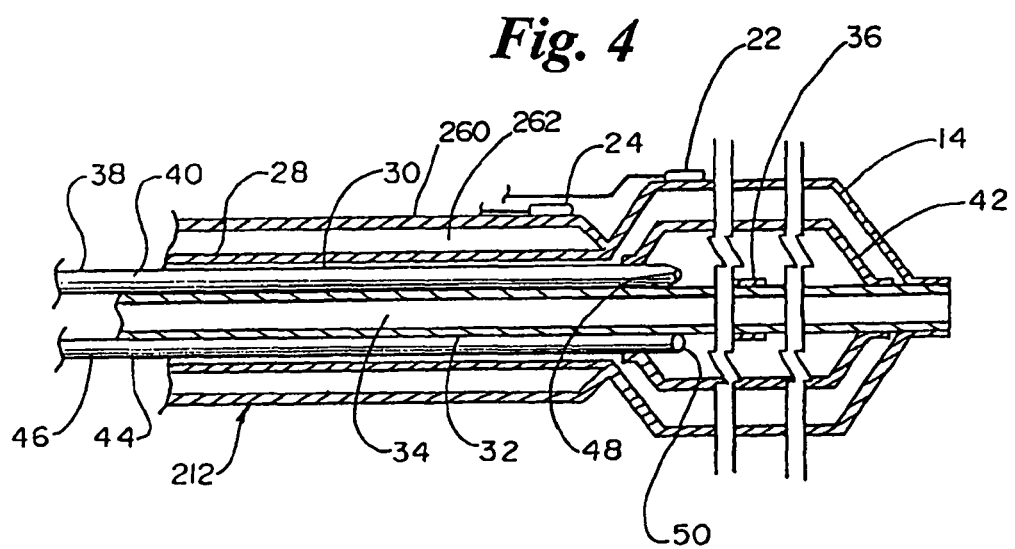
FIG. 4 is an alternative embodiment of a cryoplasty catheter in accordance with the present invention including a surrounding vacuum lumen.

Another alternate embodiment 212 of a cryoplasty catheter in accordance with the present invention is shown in FIG. 4. The cryoplasty catheter 212 is essentially similar to catheter 12 shown in FIG. 2 except that a sheath 260 surrounds tube 28 to define an annular lumen 262 between sheath 260 and tube 28. Sheath 260 preferably extends from balloon 14 proximally to manifold 16. Manifold 16 for this embodiment can include an additional port in fluid communication with lumen 262. Except for the additional port, lumen 262 should be completely sealed such that a vacuum may be maintained within lumen 262 when a vacuum source is applied to the port. A vacuum can be created in lumen 262 during the procedure to provide insulation between the coolant and the patient. Sheath 262 can be made from biocompatible materials knows to those skilled in the art of catheter construction which are sufficiently rigid to prevent lumen 262 from collapsing when a vacuum is crated therein.

In use, dilatation balloon 14 of catheter 10 is advanced across a lesion in a conventional manner. Balloon 14 is dilated by forcing fluid into balloon 14 through inflation lumen 30 with pump 18. Coolant is then released into chamber 42 from a pressurized container or pump (not shown) to cool the adjacent lesion at a rate appropriate to the treatment goals described in more detail below. The coolant is discharged from chamber 42 through exhaust or drain lumen 46. The arrow in FIG. 1 proximate the manifold 16 shows coolant being discharged to the atmosphere from lumen 46. Coolant may be collected for recycling or disposal as desired.

In a preferred embodiment of the invention, the inflation fluid is a low freezing point liquid such as an ethanol mixture. The coolant is one which will provide with appropriate heat transfer characteristics consistent with the goals of treatment. Liquid $N_2$ can be used as a general purpose coolant with catheter 10 and is particularly useful when freezing of cells within the lesion is desired. When liquid $N_2$ is used in catheter 10, it can be transported to chamber 42 in the liquid phase where it evaporates at orifice 48 and exits through lumen 46 as a gas. Freon, $N_2O$ gas and $CO_2$ gas can also be used as coolants. Other coolants could be used such as cold saline solution which would enter and exit chamber 42 as a liquid, Fluisol or a mixture of saline solution and ethanol. It is anticipated that coolants such as saline solution could be used with catheter 10 when rapid freezing of cells within a lesion is not a treatment goal. One skilled in the art would appreciate that other coolants could be used in a similar manner to achieve one or more of the treatment goals.

Temperature can be monitored by thermo-resistive sensors 22 and 24 either absolutely with pre-calibrated sensors and/or relatively between sensors 22 and 24. Depending on the treatment goals and temperature level monitored, the flow rate of the coolant into the catheter can be adjusted to raise or lower the temperature of the lesion.

The goal of cryoplasty treatment is to prevent or retard the reclosure of a dilated lesion by preventing or retarding restenosis and/or recoil of the lesion. Cooling the lesion to the near 0° C. is believed to change the characteristics of the lesions in such a way as to enhance remodeling by low pressure dilatation to prevent or retard recoil of the lesion. Further cooling to freeze the lesion is believed to create apoptosis of the lesion tissue, i.e., killing cells within the lesion.

In a preferred embodiment of the method in accordance with the present invention, a cryoplasty catheter such as one described above is used to dilate the lesion and slowly cool (for example, over a 1-5 minute period) it to reduce injury to healthy tissue while altering the plaque to be more susceptible to permanent, mechanical remodeling. The temperature of the lesion during dilatation is preferred to be about 0° C. to 20° C. such that the plaque characteristics are significantly altered, but normal healthy tissue has been injury preserved.

Alternatively or in addition to slow cooling to approximately 0° C. to 20° C. for enhanced remodeling, the lesion can be flash frozen to 0° C. to −40° C. for between 20 to 30 seconds while the balloon is still inflated. Saline or contrast injections may be utilized pre, or during freeze to prevent adjacent blood freezing from creating occlusive thrombus.

The mechanisms of restenosis and recoil are not fully understood. It is believed in the case of restenosis, that freezing and thrombus tissue injures the capillaries that supply the lesion tissue and promote muscle cell proliferation. With respect to recoil, it is believed that cooling the plaque makes it relatively very stiff and crystallized, thus being more susceptible to permanent remodeling.

Numerous characteristics and advantages of the invention covered by this document have been set fort in the foregoing description. It will be understood, however, that this disclosure is, in many respects, only illustrative. Changes may be made in details, particularly in matters of shape, size and arrangement of parts without exceeding the scope of the invention. The inventions's scope is, of course, defined in the language in which the appended claims are expressed.

A number of embodiments of the invention have been described. Nevertheless, it will be understood that various modifications may be made without departing from the spirit and scope of the invention.

What is claimed is:

1. A cryoplasty catheter, comprising:
   a shaft having proximal and distal ends, the shaft defining an inflation lumen, coolant intake lumen and exhaust lumen therethrough, each lumen having a proximal and distal end proximate the proximal and distal ends of the shaft respectively;
   a dilatation balloon disposed at the distal end of the shaft and in fluid communication with the inflation lumen; and
   a chamber disposed within the balloon and in fluid communication with the intake and exhaust lumens.

2. The cryoplasty catheter in accordance with claim 1, wherein the source of coolant connected to the proximal end of the shaft in fluid communication with the intake lumen.

3. The cryoplasty catheter in accordance with claim 2, wherein the coolant source contains liquid $N_2$.

4. The cryoplasty catheter in accordance with claim 1, further comprising a thermo-resistive sensor disposed on the dilatation balloon.

5. The cryoplasty catheter in accordance with claim 4, further comprising a second thermo-resistive sensor disposed on the shaft.

6. The cryoplasty catheter in accordance with claim 1, wherein the shaft further defines a guidewire lumen.

7. The cryoplasty catheter in accordance with claim 1, wherein the shaft is at least in part surrounded by an insulating sheath which in part defines a vacuum lumen.

8. A method of performing cryoplasty, comprising the steps of:
   advancing a dilatation balloon catheter across a lesion, the dilatation balloon catheter including a shaft having a proximal end and a distal end, the dilation balloon catheter also including a dilatation balloon disposed adjacent the distal end of the shaft;
   inflating the dilation balloon to dilate the lesion;
   delivering a coolant to the dilation balloon to cool the lesion to aid in mechanical remodeling of the lesion by dilatation; and
   freezing a portion of the lesion adjacent to the dilation balloon to kill cells within the lesion, wherein the freezing is by flash freezing for 20 to 60 seconds to enhance the effectiveness of the freezing step.

9. The cryoplasty method in accordance with claim 8, wherein the lesion adjacent the balloon is cooled to between 20° C. and 0° C. for aiding in remodeling of the lesion.

10. The cryoplasty method in accordance with claim 8, wherein the cells are frozen at a temperature of between 0° C. to −40° C.

11. The cryoplasty method in accordance with claim 8, wherein the dilatation catheter further includes a coolant intake lumen, an inflation lumen, exhaust lumen and a separate coolant chamber within the balloon to contain coolant separately from balloon inflation fluid, the chamber in fluid communication with the intake lumen and exhaust lumen.

12. A method of performing cryoplasty, comprising the steps of:
   advancing a dilatation balloon catheter across a lesion, the dilatation balloon catheter including a shaft having a proximal end and a distal end, the shaft defining a coolant intake lumen, the dilation balloon catheter having a dilatation balloon in fluid communication with the coolant inlet lumen;
   inflating the dilation balloon to dilate the lesion; and
   delivering a coolant to the dilation balloon to freeze a portion of the lesion adjacent to the dilation balloon to kill cells within the lesion, wherein the cells are frozen at a temperature of between −20° C. to −40° C.

13. The cryoplasty method in accordance with claim 12, wherein the dilatation catheter further includes an inflation lumen, exhaust lumen and a separate coolant chamber within the balloon to contain coolant separately from balloon inflation fluid, the chamber in fluid communication with the intake lumen and exhaust lumen.

14. The cryoplasty method in accordance with claim 12, further comprising the step of: delivering coolant to the balloon to cool the lesion to aid in mechanical remodeling of the lesion by dilatation.

15. The cryoplasty method in accordance with claim 14, wherein the lesion adjacent the balloon is cooled to between 10° C. and −10° C. for aiding in remodeling of the lesion.

* * * * *